(12) United States Patent
Shindo et al.

(10) Patent No.: US 8,342,002 B2
(45) Date of Patent: Jan. 1, 2013

(54) INSPECTION APPARATUS FOR SENSOR ELEMENT, AND METHOD FOR INSPECTING ELECTRICAL CHARACTERISTICS OF SENSOR ELEMENT

(75) Inventors: Hiroyuki Shindo, Kasugai (JP); Kiyotaka Sugiura, Kani (JP)

(73) Assignees: NGK Insulators, Ltd., Nagoya (JP); NGK Ceramic Device Co., Ltd., Komaki (JP)

( * ) Notice: Subject to any disclaimer, the term of this patent is extended or adjusted under 35 U.S.C. 154(b) by 75 days.

(21) Appl. No.: 12/987,220

(22) Filed: Jan. 10, 2011

(65) Prior Publication Data
US 2011/0174049 A1 Jul. 21, 2011

(30) Foreign Application Priority Data
Jan. 18, 2010 (JP) ................................. 2010-007732

(51) Int. Cl.
*G01N 1/21* (2006.01)
(52) U.S. Cl. ....................................................... 73/1.06
(58) Field of Classification Search .................. None
See application file for complete search history.

(56) References Cited

U.S. PATENT DOCUMENTS

| | | | | |
|---|---|---|---|---|
| 4,555,930 A * | 12/1985 | Leach et al. | .................... | 73/23.2 |
| 4,739,645 A * | 4/1988 | Drbal | ............................. | 73/1.06 |
| 4,961,341 A | 10/1990 | Tanaka et al. | | |
| 5,804,695 A * | 9/1998 | Dageforde | ...................... | 73/1.07 |
| 5,902,469 A | 5/1999 | Kato et al. | | |
| 6,769,285 B2 * | 8/2004 | Schneider et al. | .............. | 73/1.06 |
| 2006/0081033 A1* | 4/2006 | Peng | ............................ | 73/31.05 |
| 2007/0169535 A1* | 7/2007 | Itakura et al. | ................... | 73/1.06 |
| 2007/0186618 A1* | 8/2007 | Ackerman | ....................... | 73/1.06 |
| 2009/0095048 A1 | 4/2009 | Sakai et al. | | |
| 2010/0326165 A1* | 12/2010 | Rauworth et al. | .............. | 73/1.06 |

FOREIGN PATENT DOCUMENTS

| | | |
|---|---|---|
| JP | 53-078886 A1 | 7/1978 |
| JP | 57-208443 A1 | 12/1982 |
| JP | 3537983 B2 | 6/2004 |
| JP | 2006-284223 A1 | 10/2006 |
| JP | 2010-223860 A1 | 10/2010 |

* cited by examiner

*Primary Examiner* — Robert R Raevis
(74) *Attorney, Agent, or Firm* — Burr & Brown

(57) ABSTRACT

An inspection apparatus including a cylindrical chamber having an opening part and a bottomed end part. The chamber includes an element insertion/extraction part, a tapered part, and a gas introduction part. The element insertion/extraction part is a tubular space continuous from the opening part. The tapered part is connected to the element insertion/extraction part, and is a space having a tapered shape in a cross-sectional view sectioned perpendicularly so that a lengthwise direction is larger toward the inner side. The gas introduction part is a tubular space continuously extending from the tapered part to a bottom portion. A sensor element is inserted into the chamber such that a front end thereof reaches the tapered part while a gap is formed between the sensor element and the chamber, and in this condition, an inspection gas is supplied to the chamber through a supply port provided in the gas introduction part.

15 Claims, 5 Drawing Sheets

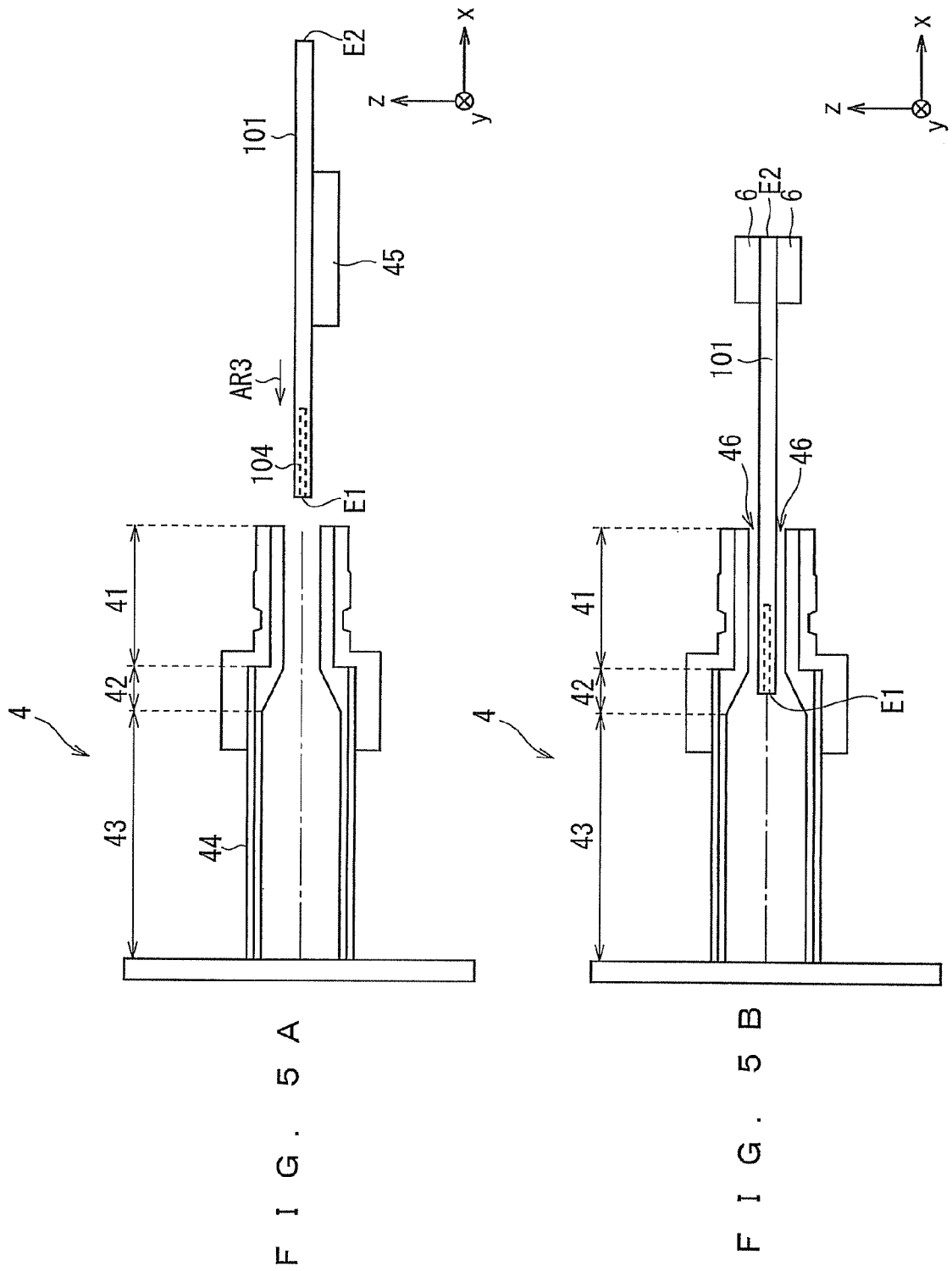

INSPECTION APPARATUS FOR SENSOR ELEMENT, AND METHOD FOR INSPECTING ELECTRICAL CHARACTERISTICS OF SENSOR ELEMENT

BACKGROUND OF THE INVENTION

1. Field of the Invention

The present invention relates to an inspection apparatus for a sensor element for use in a gas sensor, and particularly to an inspection apparatus for inspecting element characteristics in a gas atmosphere.

2. Description of the Background Art

Conventionally, various gas sensors have been used for recognizing a concentration of a desired gas component in a measurement gas. For example, as a device for measuring a NOx concentration in a measurement gas such as a combustion gas, known is a NOx sensor having a sensor element which is formed using an oxygen-ion conductive solid electrolyte such as zirconia ($ZrO_2$) (for example, see Japanese Patent Application Laid-Open No. 2006-284223 and Japanese Patent No. 3537983).

In sensor elements of gas sensors including the NOx sensors disclosed in Japanese Patent Application Laid-Open No. 2006-284223 and Japanese Patent No. 3537983, a concentration of an object component in a measurement object gas is obtained by utilizing the fact that in a case where the measurement object gas component is decomposed at a measuring electrode, the amount of oxygen ion occurring at that time is proportional to a current flowing in the measuring electrode and a reference electrode. To be specific, a concentration value of the object component is recognized as follows: a relationship (sensitivity characteristics, a concentration profile) between a concentration value and a current value (output signal value) in each individual sensor element is obtained in advance by using a mixed gas whose object component concentration is already known; and in an actual use, a measured current value is converted into a concentration value based on the sensitivity characteristics.

The above-described sensitivity characteristics are determined before each gas sensor is used (for example, before shipment), and normally dealt as fixed characteristics without being changed when the gas sensor is used afterward. This is based on the assumption that actual sensitivity characteristics do not vary during the use of the gas sensor. If the actual sensitivity characteristics change over time, the concentration value which is calculated based on the sensitivity characteristics determined at the time of shipment loses its reliability as the use of the gas sensor continues, and eventually the gas sensor loses a measurement accuracy set in its specification.

To ensure the measurement accuracy, in a manufacturing process of a sensor element, an element characteristics inspection is performed to evaluate electrical characteristics of a sensor element in an atmosphere of a mixed gas similar to a measurement gas, and if sensitivity characteristics of a sensor element vary or do not satisfy a predetermined specification (management range), it is determined that the sensor element is a defective product.

Since the sensitivity characteristics slightly differ among individual sensor elements, it is necessary to perform the element characteristics inspection on all the individual sensor elements, in order that all of gas sensors shipped as product satisfy a predetermined quality (measurement accuracy). Moreover, from the viewpoint of reliability, the element characteristics inspection has to be performed on all the sensor elements under substantially the same conditions. On the other hand, for improvement of productivity, it is demanded to shorten an inspection time by concurrently inspecting a plurality of sensor elements.

SUMMARY OF THE INVENTION

The present invention relates to an inspection of a sensor element for a gas sensor, and is directed to an inspection apparatus therefor and a method for inspecting electrical characteristics therein.

According to the present invention, an inspection apparatus for a sensor element for use in a gas sensor includes: a plurality of chambers each of which is a substantially cylindrical member having an opening part opening to the outside at one end thereof and a bottomed end part at the other end thereof, one sensor element being inserted into each of the plurality of chambers; a gas supply element which supplies a predetermined inspection gas to each of the plurality of chambers; a plurality of flow rate adjusting elements each provided so as to correspond to each of the plurality of chambers, each of the plurality of flow rate adjusting elements being operable to individually control a flow rate of the mixed gas in each of the plurality of chambers; and a measuring element which is electrically connected to a sensor element inserted into each of the plurality of chambers, and performs a predetermined electrical measurement. Each of the plurality of chambers includes: an element insertion/extraction part into and from which the sensor element is inserted and extracted; a gas introduction part to which a supply port for the inspection gas supplied from the gas supply element is connected; and a tapered part connected to each of the element insertion/extraction part and the gas introduction part. The element insertion/extraction part is a substantially tubular space continuous from the opening part. The gas introduction part is a substantially tubular space continuously extending from the tapered part to a bottom portion of the chamber. The inner diameter of the element insertion/extraction part is smaller than the inner diameter of the gas introduction part. A cross-section surface of the tapered part sectioned perpendicularly to a lengthwise direction of the chamber becomes larger from a the element insertion/extraction part side toward a the gas introduction part side.

According to the present invention, a method for inspecting electrical characteristics of a sensor element for use in a gas sensor includes the steps of: (a) preparing a chamber which is a substantially cylindrical member having an opening part opening to the outside at one end thereof and a bottomed end part at the other end thereof, the chamber including an element insertion/extraction part into and from which a sensor element is inserted and extracted, a gas introduction part to which a supply port for an inspection gas supplied from a predetermined gas supply element is connected, and a tapered part connected to each of the element insertion/extraction part and the gas introduction part; (b) inserting the sensor element into the chamber such that a front end thereof reaches the tapered part while a gap is formed between the sensor element and the chamber; (c) supplying the inspection gas from the gas supply element to the chamber through the supply port connected to the gas introduction part while the sensor element is being inserted into the chamber; and (d) performing an electrical measurement by, while supplying the inspection gas to the chamber, electrically connecting a predetermined measuring element to a terminal electrode provided near the other end of the sensor element which is inserted into the chamber. The element insertion/extraction part is a substantially tubular space continuous from the opening part. The gas introduction part is a substantially tubular space continuously extending from the tapered part to a bottom portion. The inner diameter of the element insertion/extraction part is smaller than the inner diameter of the gas introduction part, and a cross-section surface of the tapered part sectioned perpendicularly to a lengthwise direction becomes larger from a the element insertion/extraction part side toward a the gas introduction part side. In the step (d), the electrical measurement is performed while the inspection gas is being flown out through the gap.

According to these inventions, the inner diameter of the element insertion/extraction part into which the sensor element is inserted is smaller than the inner diameter of the gas introduction part provided at a more interior side. Therefore, in inspection, an inflow of an external atmosphere can be suppressed while the measurement chamber is kept opened. Particularly when the measurement is performed while the mixed gas is being flown, the inflow of the external atmosphere can be suppressed more reliably.

Hence, an object of the present invention is to provide an inspection apparatus capable of an inspection with an excellent inspection efficiency and a high reliability.

These and other objects, features, aspects and advantages of the present invention will become more apparent from the following detailed description of the present invention when taken in conjunction with the accompanying drawings.

BRIEF DESCRIPTION OF THE DRAWINGS

FIGS. 5A and 5B show a situation where the sensor element 101 is inserted into the measurement chamber 4.

DETAILED DESCRIPTION OF THE INVENTION

Outline Structure of Sensor Element

Figure 1:
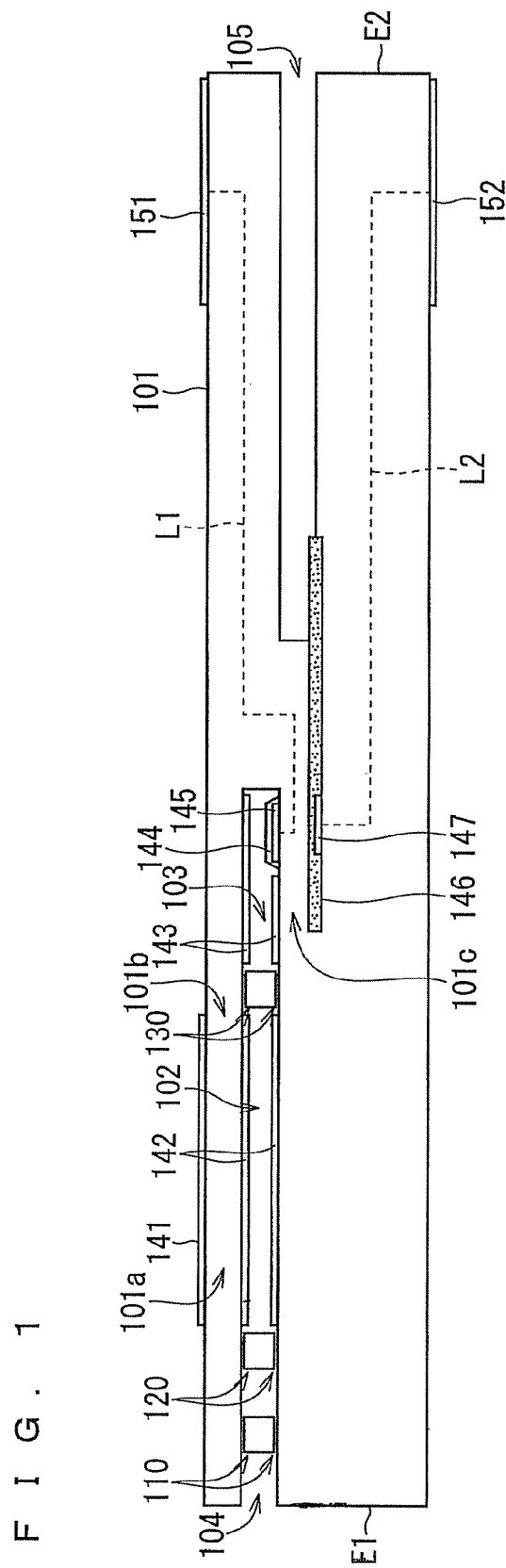
FIG. 1 is a cross-sectional view schematically showing a structure of a sensor element 101.

FIG. 1 is a cross-sectional view schematically showing a structure of a sensor element 101 which is an object to be inspected by an inspection apparatus 1 (see FIG. 2) according to this preferred embodiment. The sensor element 101 shown in FIG. 1 is a NOx sensor whose structural material is ceramic containing, as a main component, zirconia which is an oxygen-ion conductive solid electrolyte.

This sensor element 101 is a so-called tandem dual-chamber type NOx sensor element in which a first internal space 102 communicates with a gas inlet 104 opened to the external space through a first diffusion control part 110 and a second diffusion control part 120, and a second internal space 103 communicates with the first internal space 102 through a third diffusion control part 130. Calculation of a NOx gas concentration in a measurement gas using this sensor element 101 is performed in the following process.

Firstly, the measurement gas introduced into the first internal space 102 has its oxygen concentration adjusted to be substantially constant by a pumping operation (pumping in and pumping out of oxygen) of a main pumping cell which is an electrochemical pumping cell constituted by an outside pump electrode 141 provided on an outer surface of the sensor element 101, an inside pump electrode 142 provided in the first internal space 102, and a ceramic layer 101a interposed between these electrodes. Then, the measurement gas is introduced into the second internal space 103. In the second internal space 103, oxygen in the measurement gas is pumped out by a pumping operation of an auxiliary pumping cell which is similarly an electrochemical pumping cell constituted by the outside pump electrode 141, an auxiliary pump electrode 143 provided in the second internal space 103, and a ceramic layer 101b interposed between these electrodes. Thus, the measurement gas is brought into a state of sufficiently low oxygen partial pressure.

NOx in the measurement gas in this state of the low oxygen partial pressure is reduced or decomposed in a measuring electrode 145 which is provided in the second internal space 103 so as to be covered with a protective layer 144. Oxygen ion caused by this reduction or decomposition is pumped out by a measuring pumping cell which is an electrochemical pumping cell constituted by the measuring electrode 145, a reference electrode 147 provided in a porous alumina layer 146 which communicates with a reference gas inlet 105, and a ceramic layer 101c interposed between these electrodes. Based on the fact that a current value of a current (NOx current) occurring at this time and a NOx concentration has a linear relationship with each other, the NOx concentration in the measurement gas is obtained.

A heater part (not shown) is provided in the sensor element 101, and the above-described operation is performed while the sensor element 101 is being heated at a temperature of approximately 600 to 700° C. by applying a current to the heater part. Therefore, the inspection by the inspection apparatus 1 is also performed after the sensor element is heated to this temperature.

Outline Structure of Inspection Apparatus

Figure 2:
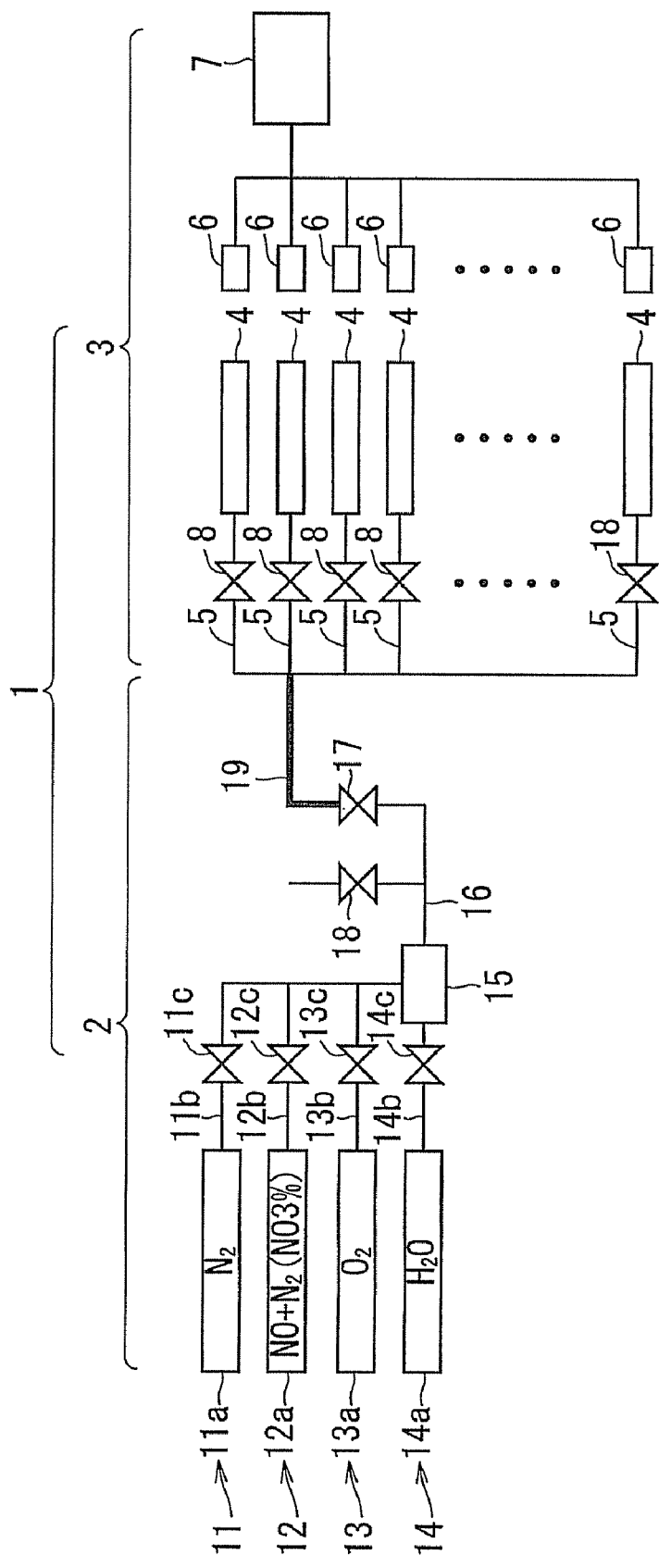
FIG. 2 shows an outline of a configuration of an inspection apparatus 1.

FIG. 2 shows an outline of a configuration of the inspection apparatus 1 according to this preferred embodiment. The inspection apparatus 1 is an apparatus for inspecting electrical characteristics (element characteristics) of the sensor element 101 used in a NOx sensor which is one type of a gas sensor. An element characteristics inspection is an inspection of electrical characteristics performed before the sensor element 101 is assembled in a main body of the NOx sensor in order to confirm that each of the above-described pumping cells, various sensor cells, and the like, has characteristics within a predetermined range that has been set as a standard.

In outline, the inspection apparatus 1 is constituted by a mixed gas supply part 2 which supplies a mixed gas which is an inspection gas at a desired mixing ratio, and a measurement part 3 which measures the sensor element 101 in an atmosphere of the mixed gas supplied from the mixed gas supply part 2.

The mixed gas supply part 2 includes a nitrogen supply system 11 which supplies a nitrogen ($N_2$) gas, a NO supply system 12 which supplies a mixed gas of NO and nitrogen gas containing NO by 3%, an oxygen supply system 13 which supplies an oxygen ($O_2$) gas, and a water supply system 14 which supplies water ($H_2O$). The supply systems have a nitrogen supply source 11a, a NO supply source 12a, an oxygen supply source 13a, and a water supply source 14a, respectively, as supply sources (chemical cylinders, tanks, or the like) of the respective substances. Supply paths 11b, 12b, 13b, and 14b from the respective supply sources are connected to a vaporizer 15. Flow rate adjusting means 11c, 12c, 13c, and 14c for adjusting flow rates of the gases in the respective supply paths are provided in the middle of the supply paths 11b, 12b, 13b, and 14b, respectively. Each of the flow rate adjusting means is configured as a valve, a mass flow controller, or the like.

In the vaporizer 15, the water supplied from the water supply system 14 is vaporized into water vapor, and mixed with the nitrogen gas, the NO gas, and the oxygen gas supplied from the other supply paths 11b, 12b, and 13b, respectively. Thereby, the mixed gas is produced. The mixed gas supplies from the vaporizer 15 to the measurement part 3 through a mixed gas supply path 16. In the middle of the mixed gas supply path 16, flow rate adjusting means 17, a leak valve 18, and the like, are appropriately provided.

A heater 19 is provided at the measurement part 3 side of the mixed gas supply path 16. The heater 19 is provided for the purpose of maintaining the temperature of the mixed gas to be supplied to the measurement part 3 for inspection at approximately 100 to 120° C.

The measurement part 3 includes a plurality of measurement chambers 4, a plurality of branch supply passages 5 each of which branches from the mixed gas supply path 16 and supplies the mixed gas to each of the measurement chambers 4, probes 6 each of which is connected to an electrode terminal of the sensor element 101 in each of the measurement chambers 4, and measuring means 7 capable of a predetermined electrical measurement through the probes 6. In the inspection apparatus 1, the separate measurement chambers 4 are used for the respective sensor elements 101. In each of the branch supply passages 5, flow rate adjusting means 8 for adjusting a flow rate of the gas in the branch supply passage 5 is provided. Thereby, the flow rate of the mixed gas in each branch supply passage 5 can be adjusted. In the measurement part 3 configured in this manner, measurements of the sensor elements 101 in the respective measurement chambers 4 can be concurrently performed. That is, in the inspection apparatus 1, a plurality of sensor elements 101 can be simultaneously inspected while using the separate measurement chambers 4 for the respective sensor elements 101. As the measuring means 7, for example, a measuring instrument capable of a measurement corresponding to what is to be inspected may be appropriated adopted.

Measurement Chamber

Figure 3A:
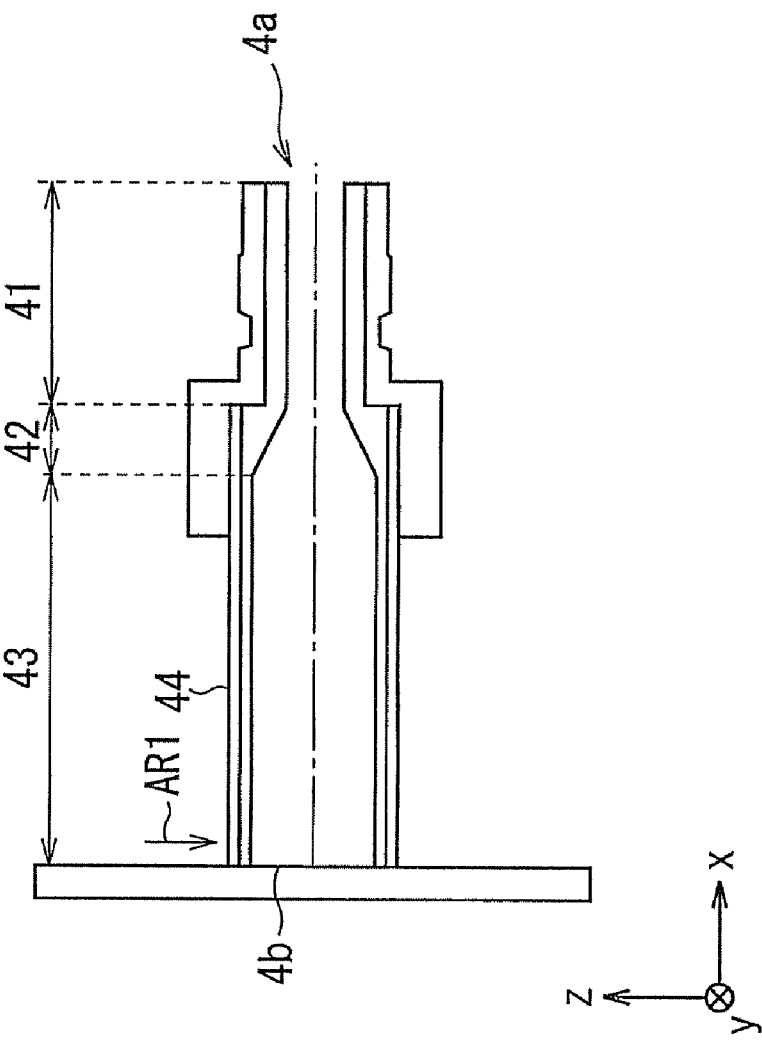
FIGS. 3A and 3B show a specific configuration of a measurement chamber 4.
Figure 3B:
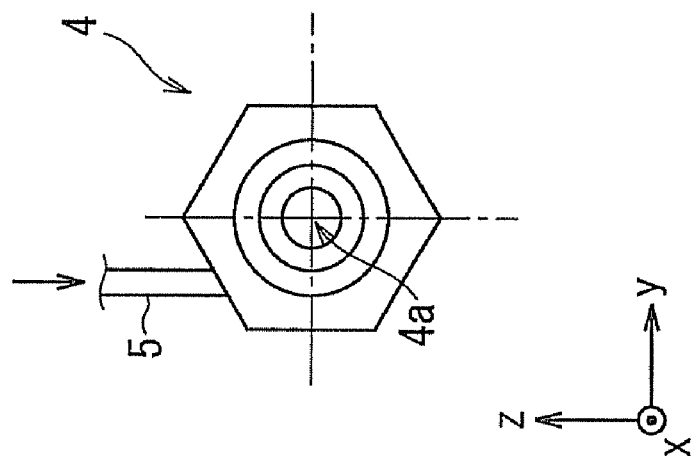

FIGS. 3A and 3B show a specific configuration of the measurement chamber 4. FIGS. 3A and 3B contain a right-hand xyz-coordinate system which defines a lengthwise direction of the measurement chamber 4 as its x-axis direction (the same applies to the subsequent drawings). FIG. 3A is a cross-sectional view along the lengthwise direction of the measurement chamber 4. FIG. 3B is a view of the measurement chamber 4 as seen from the +x side.

The measurement chamber 4 is a substantially cylindrical member which is opened to the outside at one end thereof and which has a bottom at the other end thereof. In the inside of the measurement chamber 4, an element insertion/extraction part 41, a tapered part 42, and a gas introduction part 43 are provided. The element insertion/extraction part 41 is a cylindrical space extending from an opening part 4a, and the sensor element 101 is inserted into and extracted from the element insertion/extraction part 41. The tapered part 42 is a space connected to the element insertion/extraction part 41 and having a tapered shape in a cross-sectional view whose cross section sectioned perpendicularly to the lengthwise direction increases toward the inner side (toward the −x side). The gas introduction part 43 is a cylindrical space continuous from the tapered part 42 and extending to a bottom portion 4b. In other words, the measurement chamber 4 has a configuration in which the element insertion/extraction part 41 which is a cylindrical part having a relatively smaller inner diameter and opened at an end thereof and the gas introduction part 43 which is a cylindrical part having a relatively large inner diameter and closed at an end thereof are connected by the tapered part 42.

Figure 4:
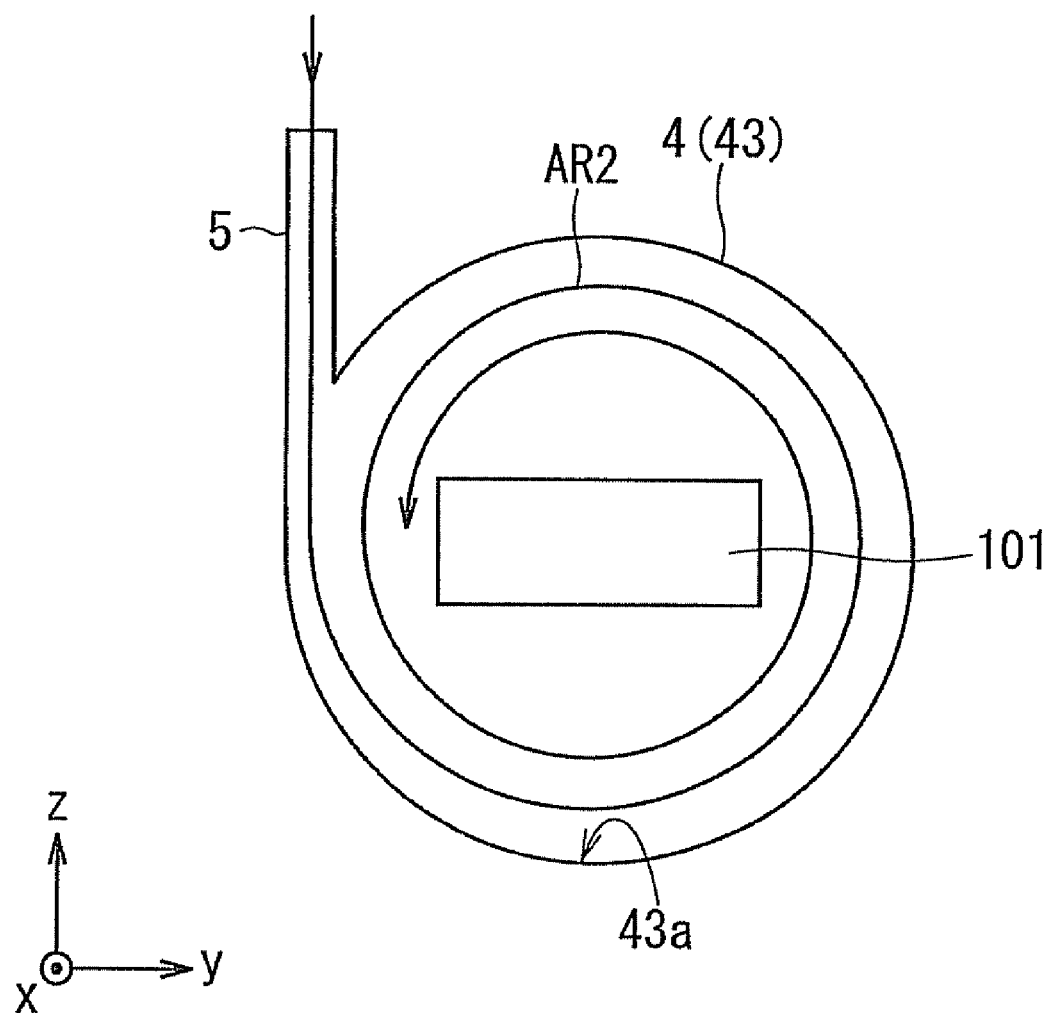
FIG. 4 shows a connection relationship between a branch supply passage 5 and a measurement chamber 4.

In the gas introduction part 43, the branch supply passage 5 is connected to the vicinity (a position indicated by the arrow AR1 of FIG. 3A) of the bottom portion 4b of the measurement chamber 4. The mixed gas is introduced into the measurement chamber 4 through this branch supply passage 5. FIG. 4 shows a connection relationship between the branch supply passage 5 and the measurement chamber 4. The branch supply passage 5 is connected to gas introduction part 43 in such a manner that the branch supply passage 5 extends in a tangential direction of an inner wall surface 43a of the gas introduction part 43. In FIG. 4, the branch supply passage 5 extends in a tangential direction of a circle which appears in a yz cross section of the gas introduction part 43. As shown in FIG. 3B, when the measurement chamber 4 is viewed from the outside, it appears as if the branch supply passage 5 is connected while being deviated toward the −y side from a zx plane (corresponding to the position of the cross section of FIG. 3A) passing through the opening part 4a.

In the measurement chamber 4, a heater 44 is provided at an outer circumferential portion extending from the tapered part 42 to the gas introduction part 43. Similarly to the heater 19, the heater 44 is provided for the purpose of maintaining the temperature of the mixed gas in the measurement chamber 4 at approximately 100 to 120° C. for the inspection.

FIGS. 5A and 5B show a situation where the sensor element 101 is inserted into the measurement chamber 4. FIG. 5A shows a situation before the sensor element 101 is inserted into the measurement chamber 4, and FIG. 5B shows a situation where the probe 6 is in contact with the sensor element 101 having inserted into the measurement chamber 4.

The sensor element 101 is inserted into the element insertion/extraction part 41 of the measurement chamber 4 as indicated by the arrow AR3 of FIG. 5A while being placed on a mounting 45 and held by holding means (not shown). More specifically, the sensor element 101 is not entirely inserted into the measurement chamber 4, but inserted into the measurement chamber 4 to such a degree that its end portion E1 at the gas inlet 104 side reaches the tapered part 42, as shown in FIG. 5B. In this state, there is a gap 46 between the sensor element 101 and the element insertion/extraction part 41. In the inspection apparatus 1 measures the sensor element 101 without closing this gap 46, that is, with this gap 46 being left opened, as will be described later. The insertion of the sensor element 101 may be realized by allowing the mounting 45 to move back and forth in the x-axis direction, or by allowing the measurement chamber 4 to move back and forth in the x-axis direction with the mounting 45 being fixed. In the latter case, the plurality of measurement chambers 4 included in the measurement part 3 may be allowed to simultaneously move back and force.

Element Characteristics Inspection

The inspection of the element characteristics by the inspection apparatus 1 is performed in each of the measurement chambers 4, while the mixed gas having a predetermined mixing ratio is being flown from the mixed gas supply part 2, in a state where the sensor element 101 is positioned in the manner shown in FIG. 5B and the probes 6 are in contact with a terminal electrode provided near an end portion E2 of the sensor element 101 at the reference gas inlet 105 side.

In this preferred embodiment, for the sake of simplification, FIG. 1 illustrates only a terminal electrode 151 and a terminal electrode 152 conducted to the measuring electrode 145 and the reference electrode 147 through a lead L1 and a lead L2, respectively, and FIG. 5B illustrates a situation where the end portion E2 of the sensor element 101 is pinched with the two probes 6 for contact with the terminal electrodes 151 and 152. However, in an actual use, the number of the terminal electrodes and the number of probes 6, and the manner of the connection are not limited thereto. A probe 6 for voltage application, a probe 6 for current passage, a probe 6 for current detection, and a probe 6 for heating the heater, which are properly prepared in accordance with a specific structure of the sensor element 101 and what is to be inspected in the element characteristics inspection, may be connected to terminal electrodes (not shown) corresponding to respective electrodes.

As the mixed gas, a first mixed gas or a second mixed gas is used. The first mixed gas is a mixed gas containing: a nitrogen ($N_2$) gas as a first main component which occupies the maximum mixing ratio (flow rate ratio); an oxygen ($O_2$) gas as a second main component which occupies the next maximum mixing ratio of approximately 10% to 18%; and a water vapor ($H_2O$) as a minor component which occupies approximately several percent of the total. The second mixed gas is a mixed gas obtained by adding approximately several hundred ppm to 1000 ppm (for example, approximately 500 ppm) of nitrogen monoxide (NO) gas to the first mixed gas. In a preferred example, the first mixed gas contains 18% of the oxygen ($O_2$) gas and 3% of the water vapor ($H_2O$), with the remainder being the nitrogen ($N_2$) gas, and the second mixed gas contains 18% of the oxygen ($O_2$) gas, 3% of the water vapor ($H_2O$), and 500 ppm of the nitrogen monoxide (NO) gas, with the remainder being the nitrogen ($N_2$) gas. This second mixed gas is similar to an exhaust gas component of an exhaust gas from an internal combustion for which the NOx sensor including the sensor element 101 performs detection.

In the inspection apparatus 1 according to this preferred embodiment, as described above, the branch supply passage 5 is provided so as to extend in the tangential direction of the inner wall surface 43a of the gas introduction part 43. Thus, roughly saying, as schematically indicated by the arrow AR2 in FIG. 4, the mixed gas supplied from the branch supply passage 5 flows spirally from the outer side to the inner side in the gas introduction part 43 (although only the rotation in the yz plane is shown in FIG. 4 for the sake of convenience, the mixed gas actually flows toward the +x side, that is, toward the near side in FIG. 4). This prevents the mixed gas introduced from the branch supply passage 5 into the measurement chamber 4 from directly jetting onto the sensor element 101, and therefore a temperature drop in the sensor element 101 during the inspection can be suppressed. Thus, the reliability of the element characteristics inspection is improved.

In the inspection apparatus 1, the gap 46 between the opening part 4a and the sensor element 101 is kept opened during the inspection, too. This raises concerns that the external atmosphere may flow into the measurement chamber 4 through the gap 46, but the inflow of the external atmosphere through the gap 46 is restricted because the inner diameter of the element insertion/extraction part 41 is smaller than the inner diameter of the gas introduction part 43. Moreover, since the mixed gas constantly flows out to the outside through the gap 46 during the inspection, the inflow of the external atmosphere through the gap 46 is suitably hindered. Thus, in the inspection apparatus 1 according to this preferred embodiment, a suitable inspection can be performed with the measurement chamber 4 being kept opened. This allows the element characteristics inspection to be performed without the effort and cost for arranging a sensor element within a sealed measurement chamber, for example. That is, improvement of the inspection efficiency can be realized.

In addition, in the inspection apparatus 1 according to this preferred embodiment, as described above, the flow rate adjusting means 8 each corresponding to each of the measurement chambers 4 are provided, which enables an individual control of a mixed gas supply state in each of the measurement chambers 4. Therefore, the element characteristics inspection can be performed concurrently on a plurality of the sensor elements 101 under the same conditions.

As has been described above, according to this preferred embodiment, the inspection apparatus which performs the element characteristics inspection of the sensor element includes a plurality of measurement chambers, and in the inspection, different measurement chambers are used for the respective sensor elements. Additionally, since the flow rate adjusting means for the mixed gas, each of which corresponds to each of the measurement chambers, are provided, the element characteristics inspection can be performed concurrently on a plurality of the sensor elements under the same conditions. Moreover, the supply path of the mixed gas is connected to the measurement chamber such that the mixed gas can flow spirally from the outer circumference side, to thereby suitably suppress a temperature drop in the sensor element which may be caused by the mixed gas supplied in the inspection. Furthermore, in the measurement chamber, the inner diameter of the element insertion/extraction part into which the sensor element is inserted is made smaller than the inner diameter of the gas introduction part. This realizes a state where during the inspection, the mixed gas flows to the outside while inflow of the external atmosphere is hindered. Thereby, the element characteristics inspection can be performed with the measurement chamber being kept opened.

Although the description above is for the inspection apparatus which inspects the element characteristics of the sensor element for used in the NOx sensor, needless to say, the configuration of the inspection apparatus according to this preferred embodiment is also applicable to other sensor elements for which an inspection in a gas atmosphere is required. In this case, the same operations and effects as those of this preferred embodiment can be obtained by, for example, appropriately selecting a component of the mixed gas in accordance with a type of the sensor element and appropriately setting the shape of the measurement chamber and a manner of contact with the probes in accordance with the shape and the structure of the sensor element.

While the invention has been shown and described in detail, the foregoing description is in all aspects illustrative and not restrictive. It is therefore understood that numerous modifications and variations can be devised without departing from the scope of the invention.

What is claimed is:

1. An inspection apparatus for a sensor element for use in a gas sensor, comprising:
   a plurality of chambers each of which is a substantially cylindrical member having an opening part opening to the outside at one end thereof and a bottomed end part at the other end thereof, one sensor element being inserted into each of said plurality of chambers;
   a gas supply element which supplies a predetermined inspection mixed gas to each of said plurality of chambers;
   a plurality of flow rate adjusting elements each provided so as to correspond to each of said plurality of chambers, each of said plurality of flow rate adjusting elements being operable to individually control a flow rate of said inspection mixed gas in each of said plurality of chambers; and a measuring element which is electrically connected to the sensor element inserted into each of said plurality of chambers, and performs a predetermined electrical measurement, wherein each of said plurality of chambers includes:
- an element insertion and extraction part into and from which said sensor element is inserted and extracted;
- a gas introduction part to which a supply port for said inspection mixed gas supplied from said gas supply element is connected; and
- a tapered part connected to each of said element insertion and extraction part and said gas introduction part, said element insertion and extraction part is a substantially tubular space continuous from said opening part opening to said tapered part, said gas introduction part is a substantially tubular space continuously extending from said tapered part to a bottom portion of said chamber, the inner diameter of said element insertion and extraction part is smaller than the inner diameter of said gas introduction part, a cross-section surface of said tapered part sectioned perpendicularly to a lengthwise direction of said chamber becomes larger from said element insertion and extraction part side toward said gas introduction part side.

2. The inspection apparatus according to claim 1, wherein said supply port for said inspection mixed gas is connected to said gas introduction part so as to extend in a tangential direction of an inner wall surface of said gas introduction part.

3. The inspection apparatus according to claim 2, wherein a structural material constituting said sensor element is ceramic containing an oxygen-ion conductive solid electrolyte as a main component, said sensor element includes:
- an internal space which is provided at one end side of said sensor element and into which a measurement gas is introduced;
- an electrochemical pumping cell which pumps out oxygen from said internal space; and
- a terminal electrode which is provided near the other end of said sensor element, and connected to an electrode of said electrochemical pumping cell, said predetermined electrical measurement is performed by electrically connecting said measuring element and said terminal electrode to each other.

4. The inspection apparatus according to claim 1, wherein a structural material constituting said sensor element is ceramic containing an oxygen-ion conductive solid electrolyte as a main component, said sensor element includes:
- an internal space which is provided at one end side of said sensor element and into which a measurement gas is introduced;
- an electrochemical pumping cell which pumps out oxygen from said internal space; and
- a terminal electrode which is provided near the other end of said sensor element, and connected to an electrode of said electrochemical pumping cell, said predetermined electrical measurement is performed by electrically connecting said measuring element and said terminal electrode to each other.

5. The inspection apparatus according to claim 1, wherein each of said plurality of chambers includes a heater which is provided at an outer circumferential portion extending from said tapered part to said gas introduction part.

6. A method for inspecting electrical characteristics of a sensor element for use in a gas sensor, comprising the steps of:

(a) preparing a chamber which is a substantially cylindrical member having an opening part opening to the outside at one end thereof and a bottomed end part at the other end thereof, said chamber including an element insertion and extraction part into and from which a sensor element is inserted and extracted, a gas introduction part to which a supply port for an inspection mixed gas supplied from a predetermined gas supply element is connected, and a tapered part connected to each of said element insertion and extraction part and said gas introduction part;

(b) inserting said sensor element into said chamber such that a front end thereof reaches said tapered part while a gap is formed between said sensor element and said opening part opening of said chamber;

(c) supplying said inspection mixed gas from said gas supply element to said chamber through said supply port connected to said gas introduction part while said sensor element is being inserted into said chamber; and (d) performing an electrical measurement by, while supplying said inspection mixed gas to said chamber, electrically connecting a predetermined measuring element to a terminal electrode provided near the other end of said sensor element which is inserted into said opening part opening of said chamber, wherein said element insertion and extraction part is a substantially tubular space continuous from said opening part opening to said tapered part, said gas introduction part is a substantially tubular space continuously extending from said tapered part to a bottom portion, the inner diameter of said element insertion and extraction part is smaller than the inner diameter of said gas introduction part, and a cross-section surface of said tapered part sectioned perpendicularly to a lengthwise direction becomes larger from said element insertion and extraction part side toward said gas introduction part side, in said step (d), said electrical measurement is performed while said inspection mixed gas is being flown out through said gap.

7. The method according to claim 6, wherein said supply port for said inspection mixed gas is connected to said gas introduction part so as to extend in a tangential direction of an inner wall surface of said gas introduction part.

8. The method according to claim 7, wherein a structural material constituting said sensor element is ceramic containing an oxygen-ion conductive solid electrolyte as a main component, said sensor element includes:
- an internal space which is provided at one end side of said sensor element and into which a measurement gas is introduced; and
- an electrochemical pumping cell which pumps out oxygen from said internal space, said terminal electrode is provided near the other end of said sensor element.

9. The method according to claim 6, wherein a structural material constituting said sensor element is ceramic containing an oxygen-ion conductive solid electrolyte as a main component, said sensor element includes:
    an internal space which is provided at one end side of said sensor element and into which a measurement gas is introduced; and
    an electrochemical pumping cell which pumps out oxygen from said internal space,
said terminal electrode is provided near the other end of said sensor element.

10. The method according to claim 6, wherein
said chamber includes a heater which is provided at an outer circumferential portion extending from said tapered part to said gas introduction part,
in said step (d), the measurement is performed while keeping a temperature of the inside of said chamber at 100 to 120° C. by said heater.

11. A method for inspecting electrical characteristics of a sensor element for use in a gas sensor by using an inspection apparatus,
    said inspection apparatus comprising:
    a plurality of chambers each of which is a substantially cylindrical member having an opening part opening to the outside at one end thereof and a bottomed end part at the other end thereof, one sensor element being inserted into each of said plurality of chambers;
    a gas supply element which supplies a predetermined inspection mixed gas to each of said plurality of chambers;
    a plurality of flow rate adjusting elements each provided so as to correspond to each of said plurality of chambers, each of said plurality of flow rate adjusting elements being operable to individually control a flow rate of said inspection mixed gas in each of said plurality of chambers; and
    a measuring element which is electrically connected to the sensor element inserted into each of said plurality of chambers, and performs a predetermined electrical measurement,
    wherein
    each of said plurality of chambers includes:
        an element insertion and extraction part into and from which said sensor element is inserted and extracted;
        a gas introduction part to which a supply port for said inspection mixed gas supplied from said gas supply element is connected; and
        a tapered part connected to each of said element insertion and extraction part and said gas introduction part,
    said element insertion and extraction part is a substantially tubular space continuous from said opening part opening to said tapered part,
    said gas introduction part is a substantially tubular space continuously extending from said tapered part to a bottom portion of said chamber,
    the inner diameter of said element insertion and extraction part is smaller than the inner diameter of said gas introduction part,
    a cross-section surface of said tapered part sectioned perpendicularly to a lengthwise direction of said chamber becomes larger from said element insertion and extraction part side toward said gas introduction part side,
said method comprising the steps of:
(a) inserting said sensor element into each of said plurality of chambers such that a front end thereof reaches said tapered part while a gap is formed between said sensor element and said opening part opening of said chamber;
(b) supplying said inspection mixed gas from said gas supply element to each of said plurality of chambers through said supply port while said sensor element is being inserted into each of said plurality of chambers;
(c) performing said electrical measurement on said sensor element by said measuring element, while said inspection mixed gas is being flown out through said gap.

12. The method according to claim 11, wherein
said supply port for said inspection mixed gas is connected to said gas introduction part so as to extend in a tangential direction of an inner wall surface of said gas introduction part.

13. The method according to claim 12, wherein
a structural material constituting said sensor element is ceramic containing an oxygen-ion conductive solid electrolyte as a main component,
said sensor element includes:
    an internal space which is provided at one end side of said sensor element and into which a measurement gas is introduced;
    an electrochemical pumping cell which pumps out oxygen from said internal space; and
    a terminal electrode which is provided near the other end of said sensor element, and connected to an electrode of said electrochemical pumping cell,
in said step (c), said predetermined electrical measurement is performed by electrically connecting said measuring element and said terminal electrode to each other.

14. The method according to claim 11, wherein
a structural material constituting said sensor element is ceramic containing an oxygen-ion conductive solid electrolyte as a main component,
said sensor element includes:
    an internal space which is provided at one end side of said sensor element and into which a measurement gas is introduced;
    an electrochemical pumping cell which pumps out oxygen from said internal space; and
    a terminal electrode which is provided near the other end of said sensor element, and connected to an electrode of said electrochemical pumping cell,
in said step (c), said predetermined electrical measurement is performed by electrically connecting said measuring element and said terminal electrode to each other.

15. The method according to claim 11, wherein
each of said plurality of chambers includes a heater which is provided at an outer circumferential portion extending from said tapered part to said gas introduction part,
in said step (c), the measurement is performed while keeping a temperature of the inside of said chamber at 100 to 120° C. by said heater.

* * * * *